(12) United States Patent
Stockinger

(10) Patent No.: US 7,159,476 B2
(45) Date of Patent: Jan. 9, 2007

(54) MEASURING DEVICE AND METHOD FOR REDUCING MEASURING ERRORS

(76) Inventor: Christian Stockinger, 921 Cheyenne Dr., Fort Collins, CO (US) 80525

( * ) Notice: Subject to any disclaimer, the term of this patent is extended or adjusted under 35 U.S.C. 154(b) by 152 days.

(21) Appl. No.: 10/506,391

(22) PCT Filed: Mar. 13, 2003

(86) PCT No.: PCT/AT03/00073

§ 371 (c)(1),
(2), (4) Date: Sep. 1, 2004

(87) PCT Pub. No.: WO03/079896

PCT Pub. Date: Oct. 2, 2003

(65) Prior Publication Data

US 2005/0103091 A1 May 19, 2005

(30) Foreign Application Priority Data

Mar. 25, 2002 (AT) ................................. A 459/2002

(51) Int. Cl.
*G01N 33/00* (2006.01)
*G01K 3/00* (2006.01)
*G06K 9/00* (2006.01)

(52) U.S. Cl. ...................... 73/865.7; 374/137; 382/124; 382/125

(58) Field of Classification Search ............... 73/865.7; 374/137; 340/5.53, 5.83; 382/124, 125; 324/692
See application file for complete search history.

(56) References Cited

U.S. PATENT DOCUMENTS 5,079,949 A * 1/1992 Tamori .................... 73/172
5,823,950 A * 10/1998 Diab et al. ................ 600/310
5,940,525 A * 8/1999 Itsumi ....................... 382/124
6,086,247 A * 7/2000 von Hollen ................ 374/137
6,181,808 B1 * 1/2001 Fukuzumi .................. 382/126

(Continued)

FOREIGN PATENT DOCUMENTS

CN 2157794 Y * 3/1997

(Continued)

OTHER PUBLICATIONS

Yamamoto, Y. et al. "Dynamic system for the measurement of electrical skin impedance" Med & Biol. Eng. & Comput. Jan. 1979, vol. 17, pp. 135-137.*

(Continued)

*Primary Examiner*—Michael Cygan
(74) *Attorney, Agent, or Firm*—Cochran Freund & Young LLC; Samuel M. Freund

(57) ABSTRACT

The invention relates to a device for determining the non precise placement of measuring sites on measuring sensors and for reducing measuring errors, which result from the movement between the measuring sites and the measuring sensors when measuring the most diverse quantities to be measured, with the aim of creating robust measuring systems for recording measured values under real or challenging conditions. The invention is characterized by: detecting whether and which sensor elements are covered and thus in contact with the site to be measured; tracking and/or adapting the sensor elements so that the contact is not interrupted even during movements, and; the resilient arrangement of the contacts for constantly maintaining the mechanical bearing pressure when measuring the electrical skin resistance. The measurement data are processed further by software that determines the area of contact from the signals from the device and from the knowledge of the arrangement of the measuring elements, and uses the completely covered sensor elements determined thereby in order to conduct measurements with the fewest possible number of errors.

32 Claims, 11 Drawing Sheets

U.S. PATENT DOCUMENTS

Figure 1:
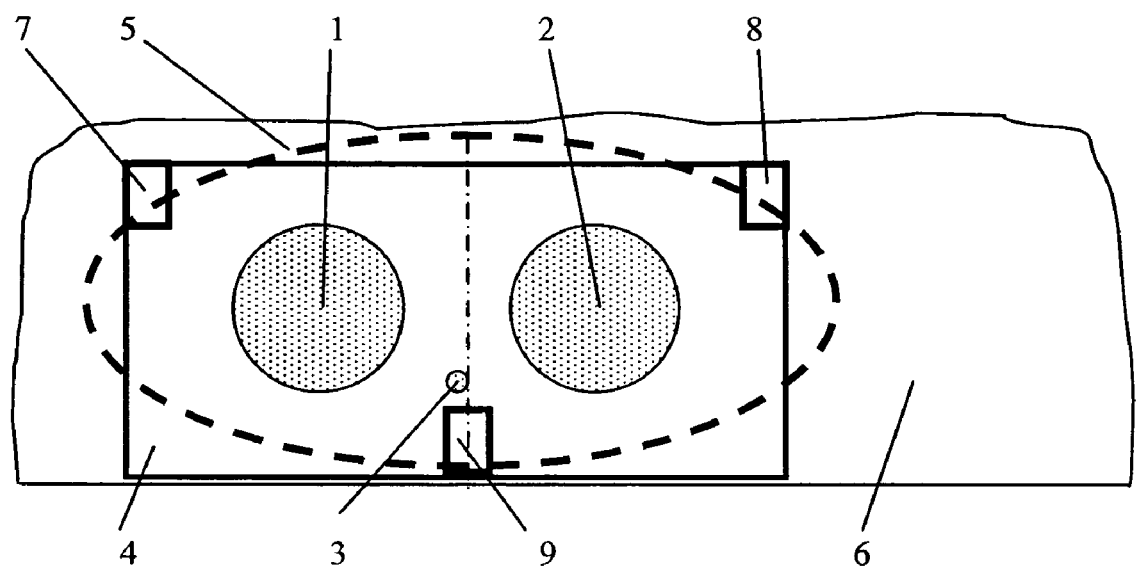

| | | |
|---|---|---|
| 6,314,315 B1 | 11/2001 | Hung et al. |
| 6,577,893 B1 * | 6/2003 | Besson et al. ............... 600/509 |
| 6,628,810 B1 * | 9/2003 | Harkin ....................... 382/116 |
| 6,633,656 B1 * | 10/2003 | Picard ........................ 382/124 |
| 6,665,428 B1 * | 12/2003 | Gozzini ...................... 382/124 |
| 6,801,799 B1 * | 10/2004 | Mendelson ................. 600/330 |
| 6,815,657 B1 * | 11/2004 | Toyoshima et al. ..... 250/214 R |
| 6,842,542 B1 * | 1/2005 | Jung .......................... 382/272 |
| 6,941,004 B1 * | 9/2005 | Goodman et al. .......... 382/124 |

FOREIGN PATENT DOCUMENTS

| | | |
|---|---|---|
| JP | 06148358 | 5/1994 |
| WO | WO 00/78209 | 12/2000 |

OTHER PUBLICATIONS

Kwok, G. et al. "Mapping Acupuncture Points Using Multi Channel Device" Australasian Physical & Engineering Sciences in Medicine, vol. 21, 1998, pp. 68-72.*

* cited by examiner

MEASURING DEVICE AND METHOD FOR REDUCING MEASURING ERRORS

CROSS REFERENCE OF RELATED APPLICATIONS

This application claims the benefit of Austrian Patent Number 410844, mt. Cl. G01D 3/028, entitled "Messvorrichtung Und Methode Zur Ermittlung Von Ungenauem Anlegen Von Sensoren Und Reduzierung Von Messfehlern Für Robuste Messsysteme Für Z.B. Physiologishe Messgrössen," filed in Austria on Mar. 25, 2002, by Christian Stockinger and PCT Application No. PCT/AT03/00073, entitled "Measuring Device And Method For Reducing Measuring Errors", filed Mar. 13, 2003, by Christian Stockinger, the entire contents of both applications are hereby specifically incorporated by reference herein for all they disclose and teach.

1:1. INTRODUCTION

The present invention applies to acquiring measuring values as accurately as possible from a testing site of interest.

Physiological values from the human or animal body (e.g. skin resistance, temperature, circulation, etc.) may be given as examples. The sensors for these values can be mounted on items like a steering device or control device, a data input device, a mobile data processing unit or a mobile telephone, which the user uses while the measurement is taken.

This has diverse applications, such as monitoring certain conditions, stress monitoring, relaxation training, fitness training, games, performance improvement, diagnostics and training of bodily functions to heal and alleviate discomfort and sicknesses, work ergonomic applications etc.

Skin resistance and temperature are the values exemplarily used to illustrate the descriptions.

As a matter of principle, other values such as circulation, oxygen saturation, surface hardness, electrical activity, heat dissipation etc. as well as values from other surfaces than the human or animal body surfaces can be measured with this invention, with a reduction of measuring errors.

The resulting measured values and the auxiliary values are measured and further processed in data processing devices.

1.2. STATE OF THE ART 1.2.1. Anticipations

As shown in patent JP11118636A (Tokai Rika Denki KK), Apr. 30th 1999 a multitude of sensor elements is used in one sensor device, the sensor elements of which are used together. Here sensors of the same type are used which are correlated with each other and whose signals are processed concertedly. From this output values are calculated, which otherwise could not be obtained from one sensor alone. The invention describes a method, to produce a well-protected and miniaturized sensor array.

The patent JP9215667A (Nippon Koden Corp.), Aug. 19th 1997 describes a multitude of sensors in a measuring device, which together deliver a summary result. For the described EKG-sensor, three kinds of sensors work together (inverting contact, not inverting contact and reference contact of an instrumentation amplifier), to measure a value from the skin as accurately as possible. The joint structure in one device allows easy manageability and reduces measuring errors.

The spring-mounted arrangement of the contacts allows an adaptation to the skin surface.

The novelty of the present invention when compared to the two anticipations is, that two kinds of sensors or two kinds of data, which can be derived from sensors, are used in a shared sensor element. In doing so one sensor's information and the known geometrical position of the sensors relative to each other are used to evaluate the correctness of the other sensor's information (if and which sensor elements have contact, if and which sensor elements are completely covered).

To further reduce measurement errors, the sensor elements are also movable and/or pliable and therefore can follow the test site during movements. Additionally, for the measurement of the skin resistance to obtain an as advantageously steady as possible bearing pressure, the contact areas or the complete sensor are spring-mounted.

1.2.2. Other Publications

The measurement of physiological values under difficult circumstances is described in DE 199 59 576 A1. It does not, however, include the special contact, coverage and complete coverage, and prevention of interrupted contact assuring mechanisms and, in the case of the skin resistance, the steady bearing pressure in the framework of such a device.

In the example of a physiological measurement on the skin in EP1 109 382 A2, assuring mechanisms are described that ensure contact through two different sensor systems. However none are described for coverage and complete coverage, prevention of interrupted contact, and in the case of skin resistance, the steady contact pressure in the framework of such a device.

As shown in U.S. Pat. No. 6,067,468, the application of the sensors is taken for granted. The users usually are advised to be sure to have a correct and steady application of sensor elements and to make as little as possible or no movements at all during the measurement.

1.3 PROBLEM

Basically, all measurement values are measured with corresponding measurement sensors. Sensors do have a geometric dimension and have to be in one way or other in contact or interaction with the testing site (corresponding to the kind of sensor element used).

While taking measurement values from a testing site which does not accurately fit the sensor elements, and/or is moving, as in the case with a user who uses a device with one or more mounted sensors, the following main problems make a simple and reliable measurement inaccurate or even impossible:

1. Problem of detecting the contact of the sensor element:

To obtain useful measured values, one has to determine whether a testing site is contacting the sensor elements at all. If the sensor has multiple sensor elements, it needs to be determined which of these sensor elements are in contact with the testing site. Therefore what needs to be detected is, whether and which sensor elements are in contact with the testing site.

2. Problem of the complete coverage of sensors:

Sensor elements have a geometric dimension, a size. This implies, that under some circumstances, especially when the testing site is not perfectly fitting the sensors or during movements, sensors will not be completely covered or not completely covered at all times by the testing site, although a contact of the testing site with the sensor elements as such is given. This leads to large measuring errors.

Further problems, preventing a simple and reliable measurement or making it impossible:

3. Problem of loosing contact during movements:

If sensor elements are completely covered and if a movement between them and the testing site occurs during the measurement, be it a movement of the sensor or be it a movement of the testing site, measuring errors can happen due to lost contact. This is the case when sensor elements are stationary on a testing site as well as when they are moved on a testing site.

4. Problem of the contact bearing pressure for skin resistance:

In the case of the physiological measuring value skin resistance, changes of the value of the skin resistance measurement signal are also possible through a change of the bearing pressure of the sensors on the skin. This happens for example through having more or less pressure of the skin onto the sensors. This leads to measuring errors in the skin resistance measurement.

The invention solves the problems described above.

INVENTION TO SOLVE THE PROBLEMS DESCRIBED ABOVE 1.4.1. Solving the problems of detecting sensor element contact and the complete coverage of the sensor elements 1.4.1.1. By means of main sensor elements and auxiliary sensor elements The invention is comprised of the following: The mounted sensor elements are divided into main sensor elements and auxiliary sensor elements. There are a number of main and auxiliary sensor elements on the sensor surface, which touches the testing site. The geometrical position of the main and the auxiliary sensor elements in relation to each other is known to the measuring system. If necessary, one or more common reference sensors can be used.

Once it has detected which auxiliary sensors the testing site touches, the measuring system can deduce the contact area. All main sensors that lie in that ascertained contact area are completely covered and their signals are used for the actual measurement. For this, and this is very favorable, the auxiliary sensor elements do not need complete coverage. This means they only need to give rough values, such as being in contact or not being in contact.

Differentiation between the signals of the main sensor elements and the signals of the auxiliary sensor elements for the data processing system has to be ensured. This can be solved for example by using direct current for the auxiliary sensors and alternating current for the main sensors. Although the electrical signals superimpose each other on the testing site they can be distinguished into signals from the auxiliary sensors and signals from the main sensors and thereby the contact area can be determined.

Alternatively, the measurements that detect the contact of the sensor elements and those accomplishing the main measurement can be done with the same measurement value and also with the same sensor elements but in consecutive measurements. In that case it is assumed that during the main measurements (between the detection measurements) the contact of the sensors with the testing site does not change.

1.4.1.1.1. Example: Thumb Sensor for a computer mouse

A thumb sensor for a computer mouse is given as an example. See FIG. 1 "schematic view of the detection of the complete coverage for the thumb sensor of a computer mouse".

To ensure that all the main sensor elements, (1) and (2) for the skin resistance and (3) for the temperature, are firstly covered and secondly covered completely, and are therefore able to fulfill their function as accurately as possible, this sensor is comprised as follows: Several auxiliary sensor elements are arranged geometrically around the main sensor elements, e.g. three (7) (8) (9). The auxiliary sensors define the contact area (5), within which the main sensor elements are located. Once it has been detected that all the auxiliary sensors are contacted, the main sensor elements (1) (2) (3), which are arranged geometrically within the contact area, are ensured to be covered and covered completely by the contacting skin surface. For this effect, the auxiliary sensors need not to be completely covered. They only need to deliver rough measurement values, like contact or no contact.

The areas created by the auxiliary sensors and the main sensor elements need not be completely overlapping. It needs only to be ensured through the design, that by covering the auxiliary sensors, the contact area for the main sensors is so large that the main sensors are lying within it and therefore are completely covered. For example, at the thumb creating a triangular area by the auxiliary sensors necessarily ensures that the main sensor elements, which extend somewhat beyond that triangular area, are correctly covered. This is because the pattern of a thumb on a sensor, which is mounted at the side of a computer mouse, is oval. If all 3 auxiliary sensors are covered, one can deduce that the main sensors, which extend somewhat beyond the triangular area, are also completely covered.

Figure 2:
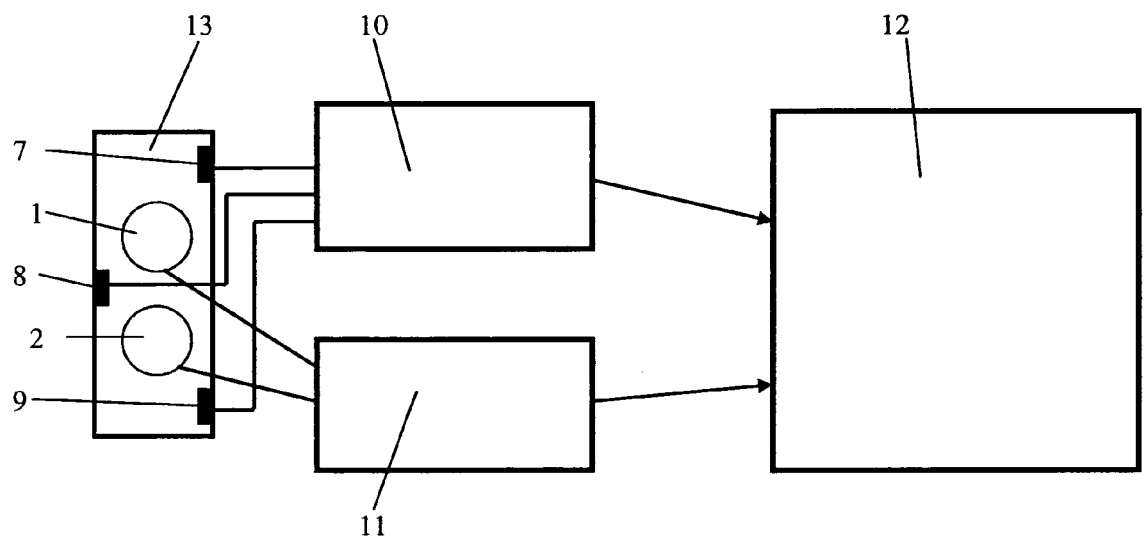

The differentiation between the signals of the main sensor elements and the signals of the auxiliary sensor elements needs to be ensured, see FIG. 2 "example of a signal flow from auxiliary sensor elements and main sensor elements for a thumb sensor of a computer mouse". In the case of this example for the measurement of the skin resistance at the thumb sensor (13) according to FIG. 1 this could be realized by utilizing a detection with alternating current (10) for the auxiliary sensor elements (7), (8), (9) and a detection with direct current (11) for the main sensor elements (1) (2). These signals are relatively easy to distinguish from each other. Auxiliary sensor elements and main sensor elements both have a measurement module whose output signals are delivered for analysis to the data processing system (12). This analysis includes the coverage detection and the measurement with completely covered main sensors.

Alternatively the measurements with the auxiliary sensors to detect the contact of the sensor elements and those accomplishing the main measurement can be done with the same measurement value in consecutive measurements. Thereby it is assumed that during the main measurements (between the detection measurements) the contact of the sensors with the testing site is not changing.

1.4.1.1.2. Example Finger Sensor

Figure 3:
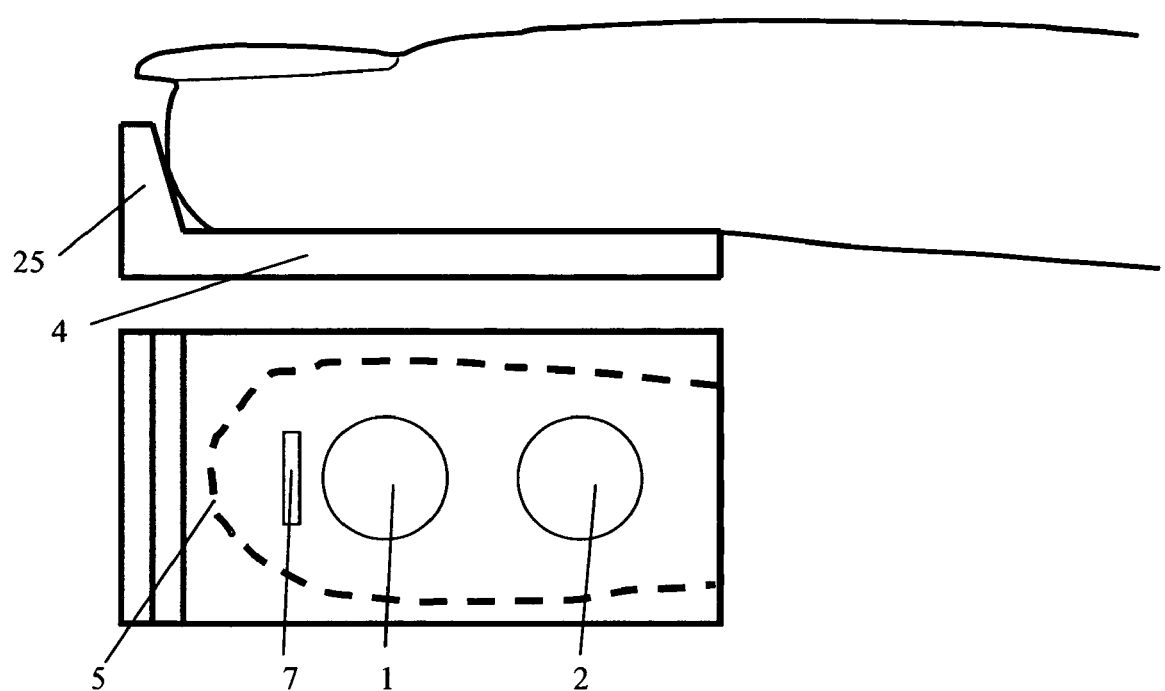

As a further example a finger sensor for a physiological measuring system according to FIG. 3 "schematic side view and upper view of a finger sensor with common reference electrode for main and auxiliary sensors" is given to explain, that the main and auxiliary sensors can have an electrode in common and that through the geometrical arrangement the complete coverage for the main measurement can be granted nevertheless.

The sensor (4) with a finger stop (25) is applied to the skin of a fingertip with its contact surface (5), the contact pattern of the contact area is oblong.

When contact is detected between the auxiliary sensor element (7) and the contact area (2) by means of a measurement, it is assured, that the main sensor element (1) is completely covered. By virtue of the knowledge of the position and the constructive size of the sensor which through the resting obstacle can only be applied to a finger tip it is assured, that the sensor element (2) is completely covered, in this case used as main sensor element as well as auxiliary sensor element, and thus a correct measurement between the sensor elements (1) and (2) can be performed.

The differentiation between the signals of the main sensor elements and the signals of the auxiliary sensor elements again can occur e.g. through the use of alternating current for the auxiliary sensor elements and through direct current for the main sensor elements.

Alternatively the measurements with the auxiliary sensor to detect the contact of the sensor elements and those accomplishing the main measurement can be done with the same measurement value (e.g. direct current) in consecutive measurements. Thereby it is assumed that during the main measurements (between the detection measurements) the contact of the sensors with the testing site is not changing.

1.4.1.1.3. Example Steering Wheel

Figure 4:
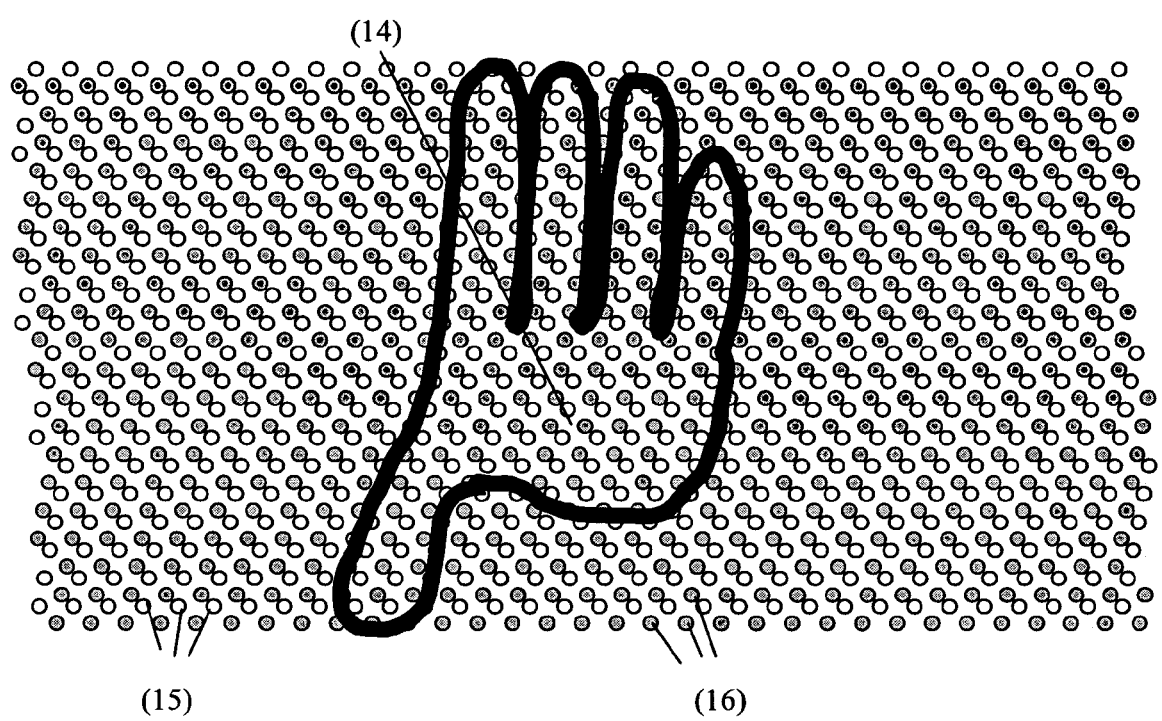

As a further example for a sensor a steering wheel with a mounted multitude of sensor elements for the measurement of skin resistance is given. In FIG. 4 "schematic view of the sensors to detect the contact area on a steering wheel" the area to touch from the steering wheel is schematically shown unrolled as rectangle. To detect which main sensor elements (15, white) are covered through the testing site skin (of the touching hand) and thus are able to fulfill their function as accurately as possible, the main sensor elements are placed between the auxiliary sensor elements (16, dotted). When it is detected which auxiliary sensors are touched by the skin, this results for the measuring system in the contact area (14). All main sensors within this contact area are completely covered and are used for the actual measurement. For this the auxiliary sensors do not need to be completely covered, they have to give only rough data such as contact or no contact.

The differentiation between the signals of the main sensor elements and the signals of the auxiliary sensor elements again can occur through e.g. the use of alternating current for the auxiliary sensor elements and through direct current for the main sensor elements. Or the measurements can be performed with the same measurement value (e.g. direct current) in consecutive measurements. Thereby it is assumed that during the main measurements (between the detection measurements) the contact of the sensors with the testing site is not changing.

1.4.1.2. By means of correlation of the sensor elements with each other

Here the sensor elements are not divided into main sensors and auxiliary sensors. The invention comprises a multitude of sensors, which are mounted on the sensor surface, which shall be touched. The geometric position of the sensor elements to each other is known to the measuring system.

To detect, which sensor elements are covered and can fulfill their function as accurately as possible this measuring device comprises, that every sensor element is sampled in the form of a matrix to detect with an auxiliary medium like current, light or the like or an other characteristic like temperature if and where a contact with the testing site takes place.

Through this procedure results the contact area of the covered sensor elements. All sensor elements within this contact area are completely covered and are used for the actual measurement. Attention needs to be applied to sensor elements at the fringe of the contact area, their measuring values are either to be rejected or, if possible, to be corrected.

The information of the position of the contact area itself can also be used for further processing.

Figure 5A:
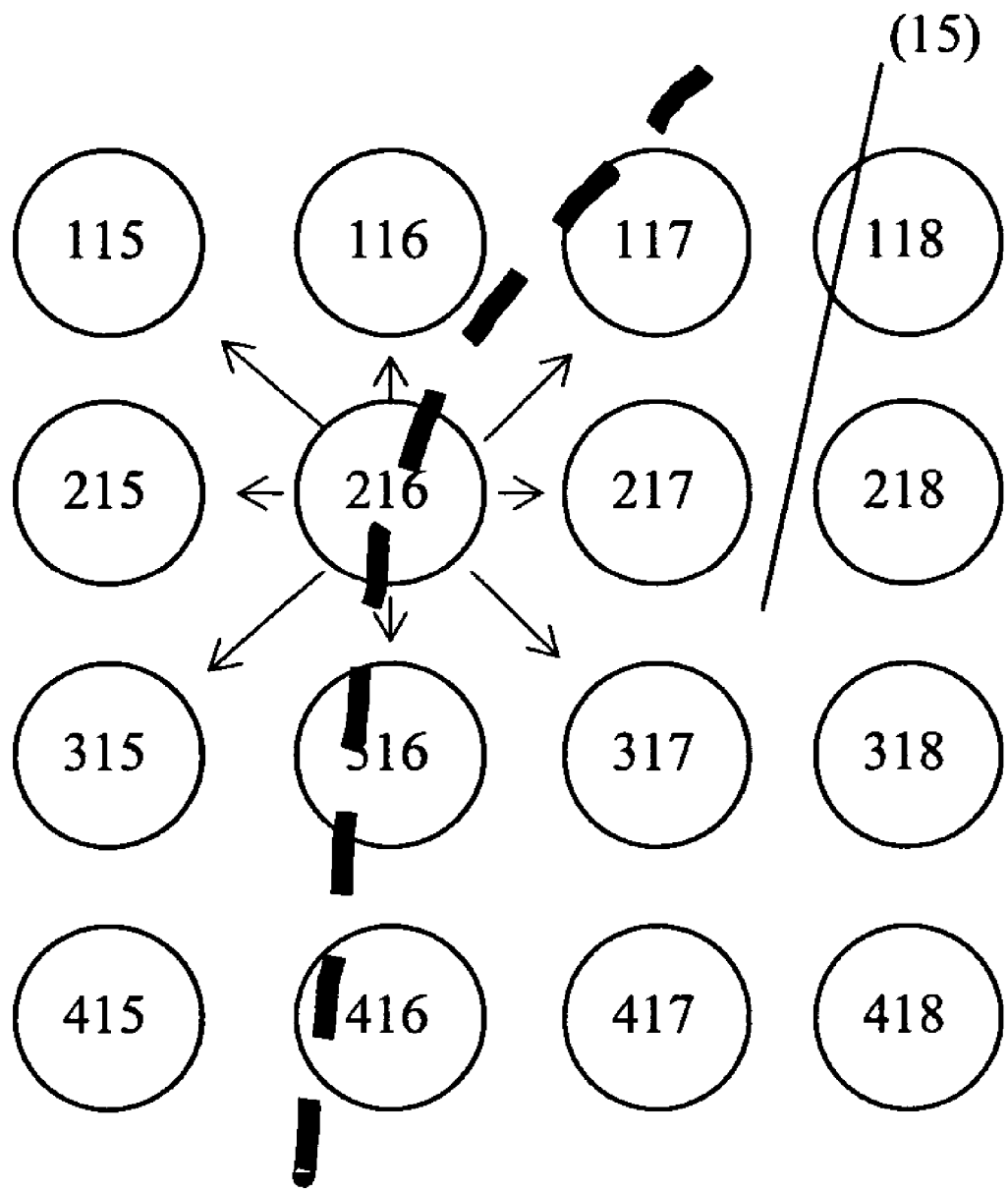

As an example again a steering wheel is given and referred to FIG. 5*a* "schematic view of the device to detect the contact area through measurements with the sensor elements to each other". Here a small part of the area to be touched is shown unrolled from the steering wheel as a rectangle, the contact area (15) touched by the skin shall be detected. The sensor elements are arranged in a matrix, e.g. 100 sensors for each row, in the figure the number of the sensor element is given in the inside of the respective sensor element. Now, with one sensor element after the other, here e.g. Nr. 216 with its geometrically surrounding elements 115, 116, 117, 215, 217, 315, 316 and 317, measurements are performed, sampled. In the example the processing of the measured values results in contact across the testing site with the elements 117, 217, 316 and 317.

With this information the system can detect, that the geometrical borderline of the testing site runs through the elements 117, 216, 316 and (after a measurement with element 316 and its surrounding elements) 416.

Figure 5B:
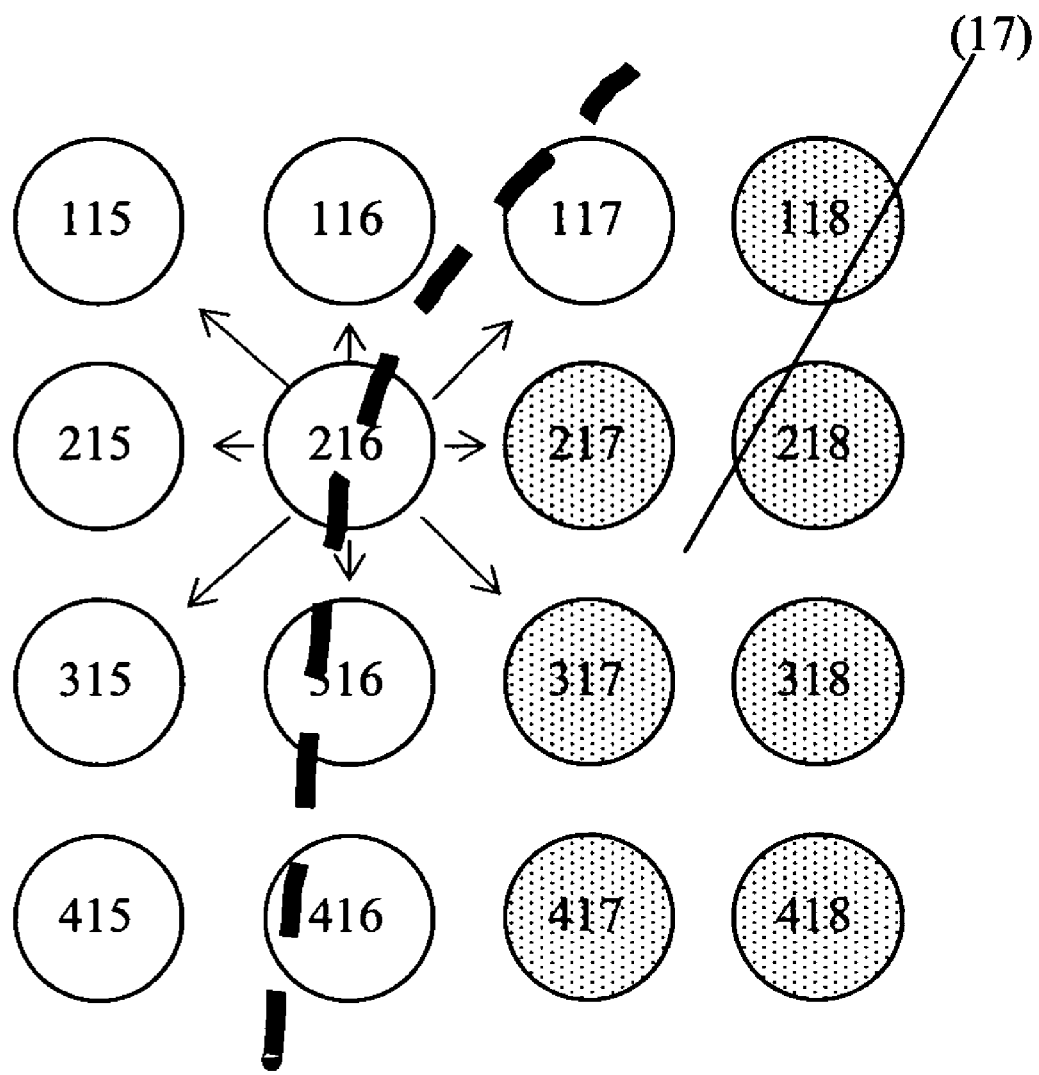

The detected contact area (17, dotted colored sensor elements) in FIG. 5*b* "schematic view of the contact area after the coverage detection with measurements of the elements to each other" with completely covered sensors is therefore detected to be to the right from the dotted sensors 118, 217, 218, 317, 318, 417, 418. After the performance of all measurements of all sensor elements with their respective surrounding sensor elements the complete contact area can be detected. With this information the actual main measurement is performed as accurately as possible during which it is assumed that the contact area is not changing. In addition, if necessary, the information about the position of the contact area is processed.

As a variation the sampling for each sensor element can be performed as a measurement with one or more common reference electrodes. Any covered sensor element can be used as reference electrode. These reference electrodes could even be designated during a measurement, when in a first measurement sequence one or more covered sensor elements are detected which are used as reference electrodes for the next measurement sequence.

1.4.2. Solution of the problem of losing contact during movements through tracking or molding of the sensor elements The sensor elements need to make good contact with the testing site, the contact needs to be warranted (sensor stationary on one testing site or moving on a testing site). In the case of the first contact and movement during the measurement this is solved by the invention by tracking and/or a molding of the sensor elements.

Therefore the invention comprises tracking the sensor elements as far as possible according to the movements to be expected in order to not lose contact with the testing site and thus to avoid measuring errors.

In addition or alternatively the invention comprises that sensor elements themselves can be formed to the form of the testing site to warrant a correct contact. Thereby the sensor elements are pliable and/or track-able and thus fit to the testing site, even during movements.

This can be done with and without using a fixed matrix of auxiliary sensors. Here the auxiliary sensors are designed as being not moveable and serve as counter bearing to bear the mechanical forces of the testing site.

1.4.2.1. Example rocker for a thumb sensor of a computer mouse

Figure 6:
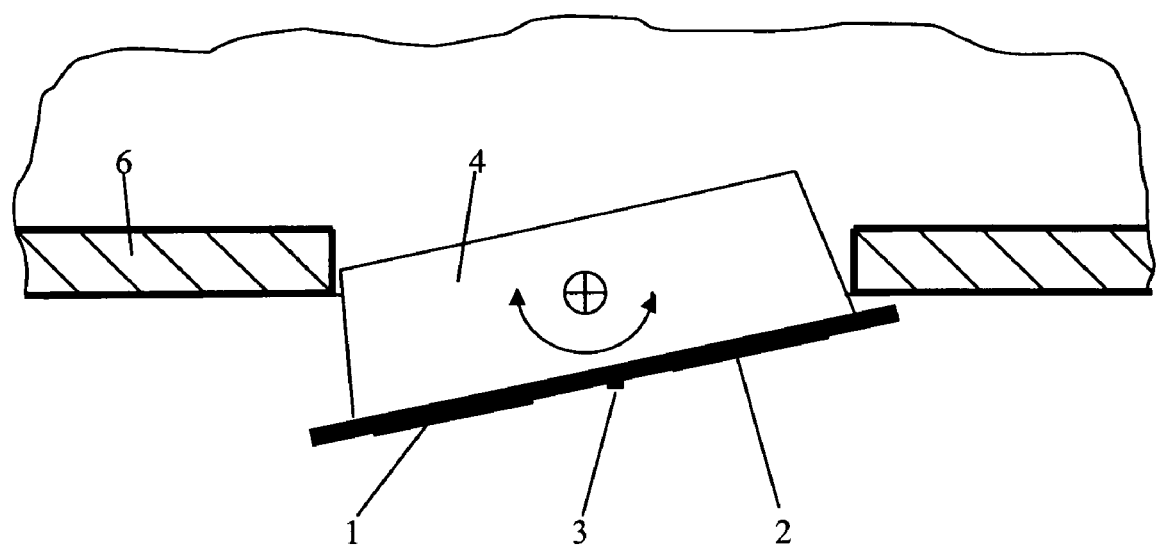

In FIG. 6 "view of a moving device with sensor elements for tracking" the sensor elements (1), (2) for the skin resistance and (3) for the temperature are built into the vertical surface of a moving device (4) (a teeter). This teeter is inserted into the PC-mouse (6) in the region of the thumb and follows the thumb in his movements during work with the PC-mouse. Through this tracking the contact between sensor elements and skin is granted within a wide range.

Figure 7:
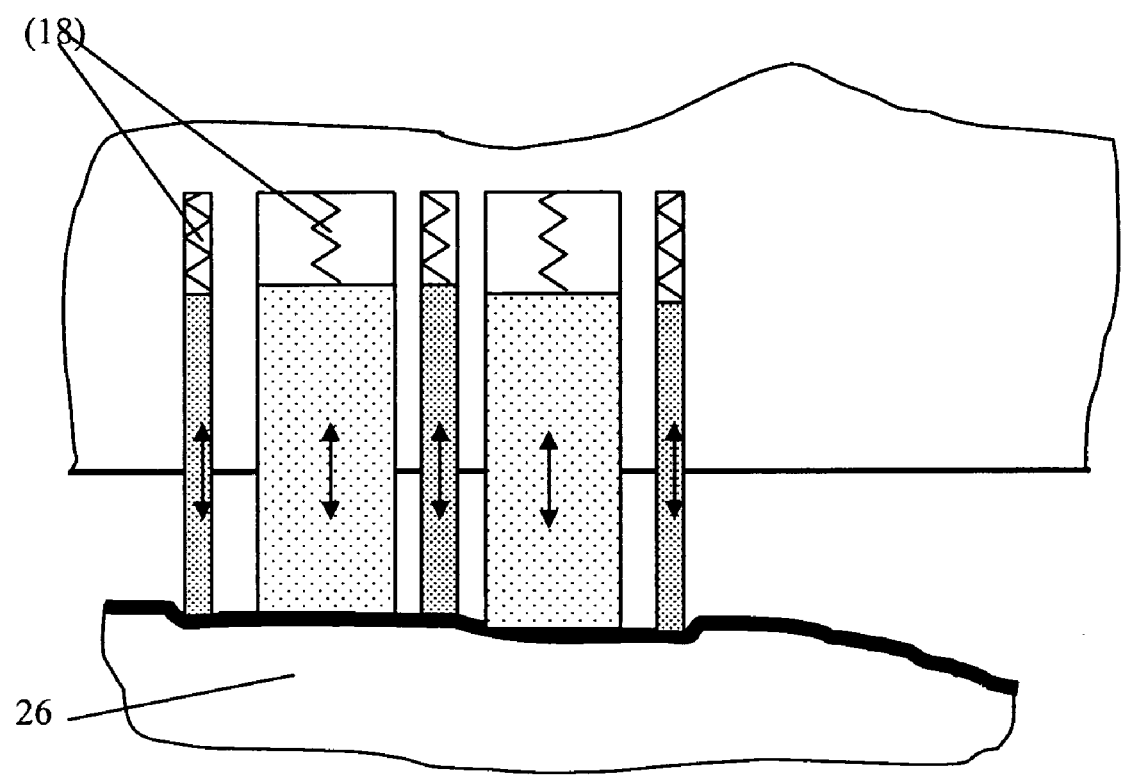

Alternatively or additionally the sensor elements (1), (2), (3) can be adjusted to the surface form of the skin to grant a correct contact to the skin, see FIG. 7 "view onto moveable sensor elements for adjusting to the testing site". Here the sensor elements are moving and equipped with springs (18) and adjust themselves to the skin (26), even during movements.

Alternatively or additionally the sensor elements (1), (2), (3) themselves can be adjusted to the surface form of the skin to assure a fitting contact to the skin. Here the sensor elements themselves are pliable. With a lightpressure they take on the form of the skin site and adjust themselves to the skin even during movements. For this the material of the sensor elements has to be pliable.

1.4.2.2. Examples of application at joysticks, game consoles, mobile data processing units and mobile telephones A joystick is a computer input device operated like a control stick of an airplane, a game console is usually used to control electronic games with input buttons.

Figure 8:
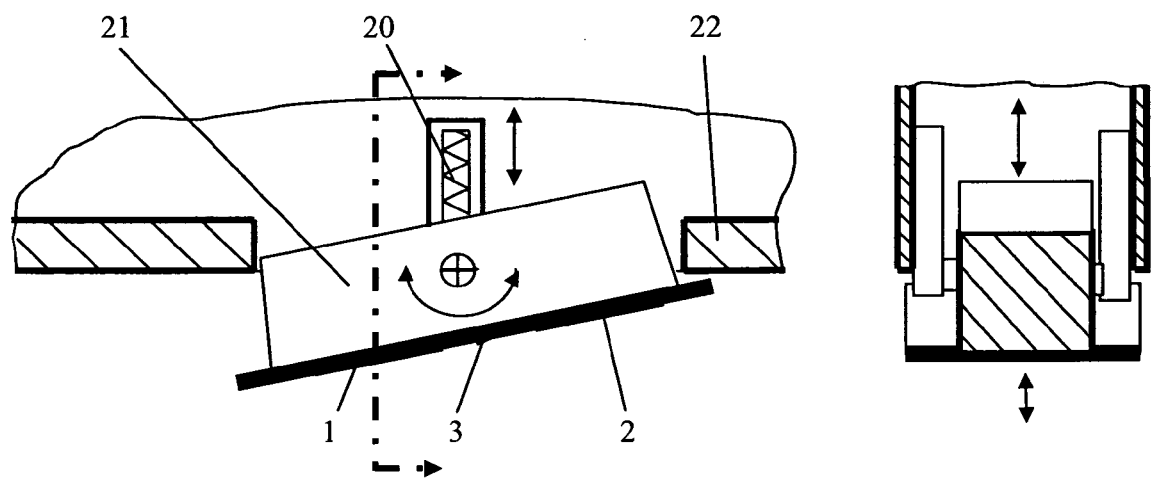

According to FIG. 8 "view onto a moving, spring-mounted device with sensor elements for tracking and in the case of the skin resistance for keeping the pressure constant", in this example sensor elements are inserted in a moving device. This is here a teeter (22), which can be pressed inwards along a vertical guide, which is spring-mounted by the spring (20). This sensor is for example inserted into the joystick (22), the mobile data processing unit or the mobile phone in the area of the heel of the hand and follows the skin during movements as it is used.

Alternatively or additionally the sensor elements (1), (2), (3) themselves can be adjusted to the surface form of the skin to grant a correct contact to the skin, similar as in FIG. 7 for the computer mouse. Here the sensor elements are pliable and/or spring-mounted moveable and thus adjust to the skin, even during movements.

For not so strict demands on the precision of the measurement the tracking can be omitted, the sensor elements then are integrated in a not moveable manner (e.g. in the region of the device which reaches the palm of the hand).

1.4.3. solution of the bearing pressure problem through keeping the pressure constant for the skin resistance measurement A factor in measuring the electric resistance of the skin is the pressure the contact areas bear onto the skin. If this pressure changes during the measurement by a more or less firm grip of the user, changes in the data of the electrical auxiliary physical value to register the skin resistance can occur, which are not caused by a change of the skin resistance (measuring error). Therefore the invention comprises spring-mounted contact areas for the skin resistance. Changes of pressure of the skin site are transferred to the material surrounding the spring-mounted contact areas. Therefore the bearing pressure of the contact areas onto the skin depends in a wide range only on the spring, which produces a constant bearing pressure.

Figure 9:
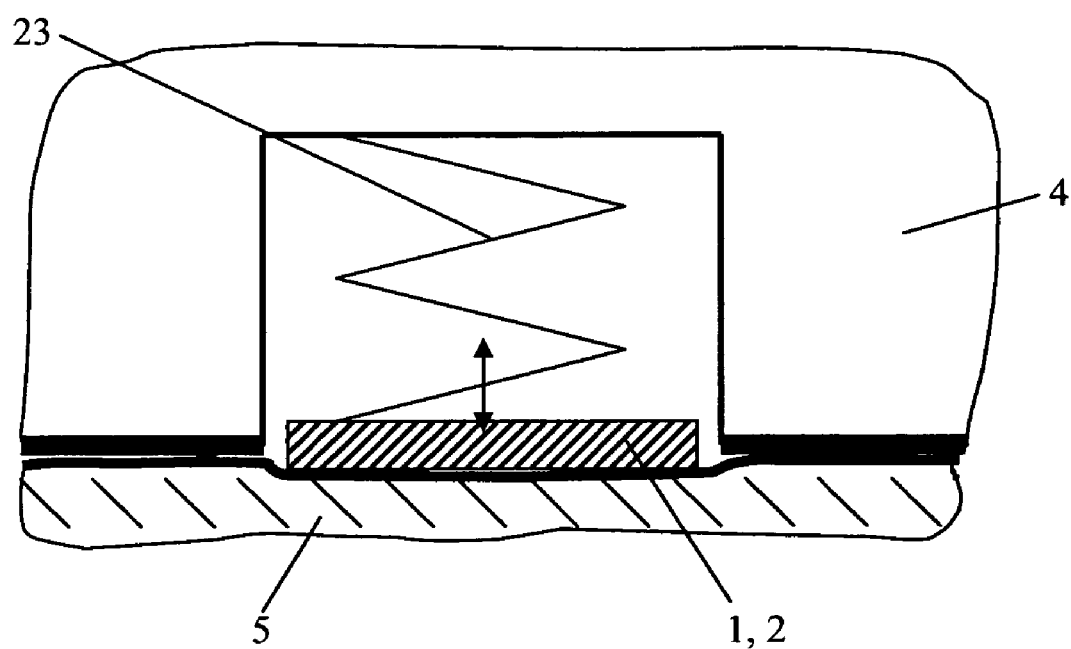

In FIG. 9 "spring-mounted contact areas for the skin resistance measurement" the spring-mounted sensor elements (1) or (2) are assembled in the sensor (4) onto which the skin (5) presses. Through the spring (23) the constant bearing pressure of the main sensors is created, hereby enabling the main sensor to measure as accurately as possible. Pressure changes are transferred only to the surrounding sensor material (4).

Figure 10:
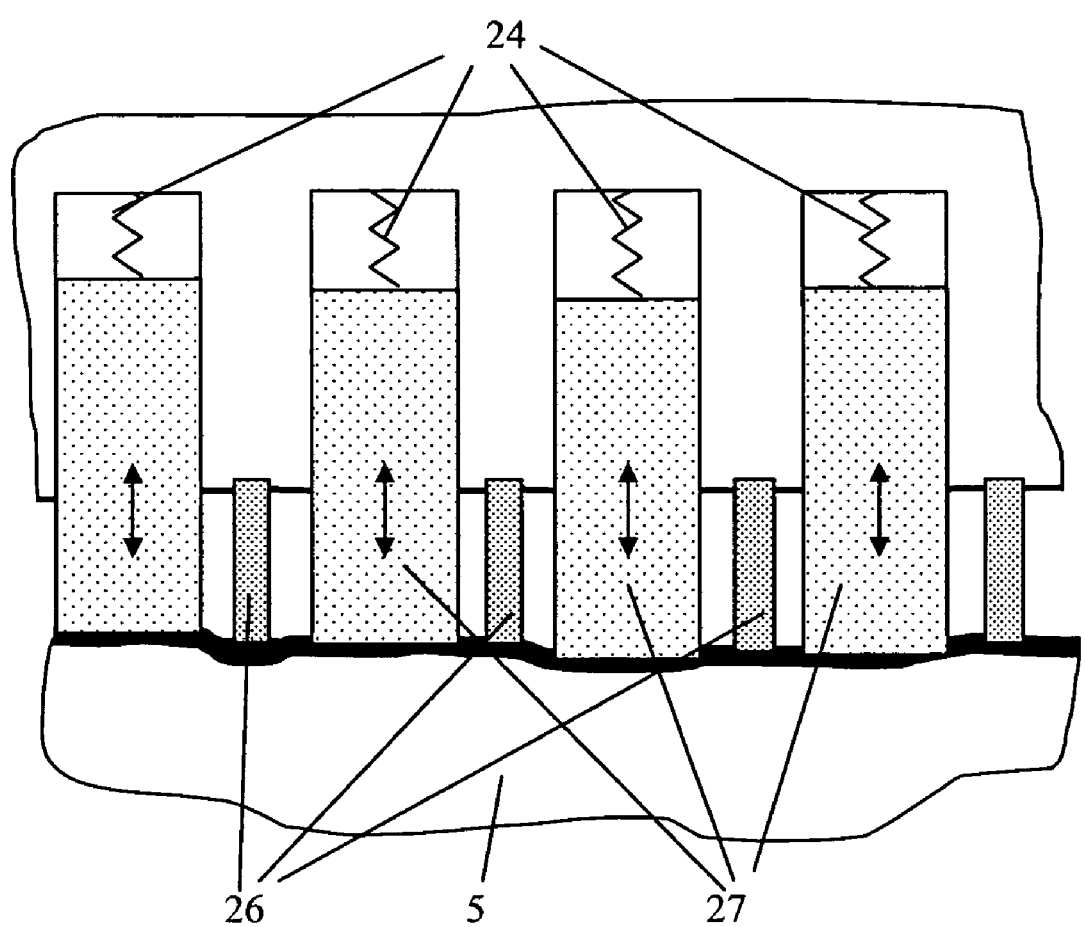

In the example according to FIG. 10 "spring-mounted contact areas for the measurement in a fixed matrix of auxiliary sensors to keep the bearing pressure constant during measurement of the skin resistance" this can be performed with a fixed matrix of auxiliary sensors. Here the skin (5) is positioned through the fixed auxiliary sensors (26, narrowly dotted), onto which the changes in pressure are transferred. For the measuring signals of the auxiliary sensors the constant bearing pressure is not so important as long as they are contacted at all. The (dotted) main sensors (27) are pressed against the skin with the springs (24). Through the positioning of the skin (5) through contacting the auxiliary sensors a constant bearing pressure results for the main sensors which now can measure with a constant bearing pressure as accurately as possible.

Alternatively the invention comprises a spring-mounting of the complete sensor element to keep the bearing pressure constant. If the skin site can only be in a defined area it is possible by tracking the complete sensor element to keep the bearing pressure constant within certain limits and thus to keep the measuring errors small.

An example would be a joystick whose spring-mounted element according to FIG. 8 reaches the skin with a somewhat constant bearing pressure as long as the hand encloses the joystick.

STRUCTURE OF THE ANALYZING SOFTWARE

This describes the structure of software in a data processing unit, which processes the measuring data of the error reducing measuring sensors.

1.5.1. Detection of coverage with auxiliary sensor elements

The analyzing software for the measuring error reducing sensors comprises, that the contact area can be determined through the coverage detection according to chapter 1.4.1.1. Along with the positioning of the sensor elements known to the system the states "no main and auxiliary sensor element covered", "certain main and auxiliary sensors covered but not completely" and "certain main and auxiliary sensor elements completely covered" can be distinguished.

In the states "no main and auxiliary sensor element covered" and "certain main and auxiliary sensors covered but not completely" the measuring data is rejected or, if possible, corrected, and thus measuring errors eliminated, furthermore a warning can be given to the user and/or an action to correct the sensors can be demanded, and the geometric position of the contact area can be processed further.

In the state "certain main and auxiliary sensor elements completely covered" the detected covered sensor elements can be used for measurements, which are as accurate as possible, and the geometric position of the contact area can be processed further.

1.5.2. Coverage detection of the sensor elements to each other

The analyzing software for the sensors with measurement error reducing through the coverage detection to each other comprises that the contact area can be determined through the coverage detection according to chapter 1.4.1.2. With the positioning of the sensor elements, which is known to the system it can distinguish between the states "no sensor elements covered" and "certain sensor elements covered and thus completely covered".

In the state "no sensor elements covered" the measuring data is rejected or, if possible, corrected, and thus measuring errors eliminated, furthermore a warning can be given to the user and/or an action to correct the sensors can be demanded.

In the state "certain sensor elements covered and thus completely covered" the detected covered sensor elements can be used for measurements as accurately as possible, and the geometric position of the contact area can be processed further.

The invention claimed is:

1. Apparatus for measuring the electrical resistance of a portion of skin, and for detecting imprecise placement of the portion of skin onto sensors adapted for such measurements and disposed on a surface of said apparatus, said apparatus comprising in combination:
   at least two main sensors disposed on the surface and defining an area thereon, said at least two main sensors being capable of measuring electrical resistance;
   at least two auxiliary sensors disposed on the surface and outside of the area defined by said at least two main sensors, said at least two auxiliary sensors being capable of measuring electrical resistance; and
   a processor for receiving and for analyzing measured electrical resistance from said at least two main sensors and from said at least two auxiliary sensors when the portion of skin is placed in contact with said apparatus; whereby a measured electrical resistance from said at least two main sensors is used in the measurement of the electrical resistance of the portion of skin only if said at least two auxiliary sensors have a measured electrical resistance.

2. The apparatus of claim 1, wherein the measured electrical resistance of said at least two main sensors is obtained using a direct current, and the measured electrical resistance of said at least two auxiliary sensors is obtained using an alternating current.

3. The apparatus of claim 1, wherein said processor differentiates between the measured electrical resistance of said at least two main sensors and the measured electrical resistance of said at least two auxiliary sensors.

4. The apparatus of claim 3, wherein said processor provides a warning if said at least two auxiliary sensors do not have a measured electrical resistance.

5. The apparatus of claim 1, wherein each of said at least two main sensors, and each of said at least two auxiliary sensors are capable of conforming to the shape of the portion of skin undergoing measurement.

6. The apparatus of claim 5, wherein each of said at least two main sensors and each of said at least two auxiliary sensors are spring-mounted to the surface such that a constant bearing pressure of the portion of skin is produced on each of said at least two main sensors and on each of said at least two auxiliary sensors.

7. The apparatus of claim 5, wherein each of said at least two main sensors are spring-mounted to the surface such that a constant bearing pressure of the portion of skin is produced on each of said at least two main sensors.

8. The apparatus of claim 5, wherein each of said at least two main sensors and each of said at least two auxiliary sensors are pivotably mounted to the surface.

9. Apparatus for measuring the electrical resistance of a portion of skin, and for detecting imprecise placement of the portion of skin onto sensors adapted for such measurements and disposed on a surface of said apparatus, said apparatus comprising in combination:
   a plurality of sensor pairs disposed on the surface, each sensor pair in said plurality of sensor pairs being capable of measuring electrical resistance; and
   a processor for receiving and for analyzing the measured electrical resistance from each of said sensor pairs in said plurality of sensor pairs, when the portion of skin is placed in contact with said apparatus; whereby measurements of the electrical resistance from sensor pairs which are in partial contact with the portion of skin are used to define a contact area, and the measurement of the electrical resistance by sensor pairs within the contact area are used in the measurement of the electrical resistance of the portion of skin.

10. The apparatus of claim 9, wherein each sensor in said pair of sensors in said plurality of pairs of sensors is capable of conforming to the shape of the portion of skin undergoing measurement.

11. The apparatus of claim 10, wherein each sensor in said pair of sensors in said plurality of pairs of sensors is spring-mounted to the surface such that a constant bearing pressure of the portion of skin on each of said sensors is produced.

12. The apparatus of claim 10, wherein each sensor in said pair of sensors in said plurality of pairs of sensors is pivotably mounted to the surface.

13. Apparatus for measuring at least one chosen property of a portion of skin, and for detecting imprecise placement of the portion of skin onto sensors adapted for such measurements and disposed on a surface of said apparatus, said apparatus comprising in combination:
   at least one main sensor disposed on the surface and defining an area thereon, said at least one main sensor having an electrical output responsive to a first skin property being measured;
   at least one auxiliary sensor disposed on the surface and outside of the area defined by said at least one main sensor, said at least one auxiliary sensor having an electrical output responsive to a second skin property being measured; and
   a processor for receiving and for analyzing the electrical output from said at least one main sensor and from said at least one auxiliary sensor when the portion of skin is placed in contact with said apparatus; whereby the electrical output from said at least one main sensor is analyzed and used in the measurement of said chosen property only if said at least one auxiliary sensor has an electrical output.

14. The apparatus of claim 13, wherein the first skin property and the second skin property are the same.

15. The apparatus of claim 13, wherein the at least one chosen property is selected from the group consisting of skin temperature, circulation, oxygen saturation, surface hardness, and heat dissipation.

16. The apparatus of claim 13, wherein each of said at least one main sensor, and each of said at least one auxiliary sensor are capable of conforming to the shape of the portion of skin undergoing measurement.

17. The apparatus of claim 16, wherein each of said at least one main sensor and each of said at least one auxiliary sensor are spring-mounted to the surface such that a constant bearing pressure of the portion of skin is produced on each of said at least one main sensor and on each of said at least one auxiliary sensor.

18. The apparatus of claim 16, wherein each of said at least two main sensors are spring-mounted to the surface such that a constant bearing pressure of the portion of skin is produced on each of said at least two main sensors.

19. The apparatus of claim 16, wherein said at least one main sensor and said at least one auxiliary sensor are pivotably mounted to the surface.

20. Apparatus for measuring a chosen property of a portion of skin, and for detecting imprecise placement of the portion of skin onto sensors adapted for such measurements and disposed on a surface of said apparatus, said apparatus comprising in combination:
  a plurality of sensors disposed on the surface, each sensor in said plurality of sensors having an electrical output responsive to the skin property being measured; and
  a processor for receiving and for analyzing the electrical output from each sensor in said plurality of sensors, when the portion of skin is placed in contact with said apparatus; whereby measurements of the electrical output from said sensors which are in partial contact with the portion of skin are used to generate a contact area, and the measurement of the electrical output by said sensors within the contact area are used in the measurement of the chosen property of the portion of skin.

21. The apparatus of claim 20, wherein the chosen property is selected from the group consisting of skin temperature, circulation, oxygen saturation, surface hardness, and heat dissipation.

22. The apparatus of claim 20, wherein each of said sensors in said plurality of sensors is capable of conforming to the shape of the portion of skin undergoing measurement.

23. The apparatus of claim 22, wherein each of said sensors in said plurality of sensors is spring-mounted to the surface such that a constant bearing pressure of the portion of skin is produced on each of said sensors in said plurality of sensors.

24. The apparatus of claim 22, wherein each of said sensors in said plurality of sensors is pivotably mounted to the surface.

25. Apparatus for measuring the electrical resistance of a portion of skin, and for detecting imprecise placement of the portion of skin onto sensors adapted for such measurements and disposed on a surface of said apparatus, said apparatus comprising in combination:
  at least one main sensor disposed on the surface and defining an area thereon;
  at least one auxiliary sensor disposed on the surface and outside of the area defined by said at least one main sensor;
  at least one reference sensor, wherein said at least one main sensor and said at least one auxiliary sensor are capable of measuring electrical resistance in cooperation with said at least one reference sensor.
  a processor for receiving and for analyzing measured electrical resistance from said at least one main sensor and from said at least one auxiliary sensor in cooperation with said at least one reference sensor when the portion of skin is placed in contact with said apparatus; whereby a measured electrical resistance from said at least one main sensor is used in the measurement of the resistance of the portion of skin only if said at least one auxiliary sensor has a measured resistance.

26. The apparatus of claim 25, wherein the measured resistance of said at least one main sensor is obtained using a direct current, and the measured resistance of said at least one auxiliary sensor is obtained using an alternating current.

27. The apparatus of claim 25, wherein said processor differentiates between the measured resistance of said at least one main sensor and the measured resistance said at least one auxiliary sensor.

28. The apparatus of claim 27, wherein said processor provides a warning if said at least one auxiliary sensor does not have a measured resistance.

29. The apparatus of claim 25, wherein said at least one main sensor, said at least one auxiliary sensor, and said at least one reference sensor are capable of conforming to the shape of the portion of skin undergoing measurement.

30. The apparatus of claim 29, wherein said at least one main sensor, said at least one auxiliary sensor, and said at least one reference sensor are spring-mounted to the surface such that a constant bearing pressure of the portion of skin is produced on said at least one main sensor, on said at least one auxiliary sensor, and on said at least one reference sensor.

31. The apparatus of claim 29, wherein said at least one main sensor and said at least one reference sensor are spring-mounted to the surface such that a constant bearing pressure of the portion of skin is produced on said at least one main sensor and on said at least one reference sensor.

32. The apparatus of claim 29, wherein said at least one main sensor, said at least one auxiliary sensor, and said at least one reference sensor are pivotably mounted to the surface.

* * * * *